(12) United States Patent
Watt

(10) Patent No.: US 6,686,500 B1
(45) Date of Patent: Feb. 3, 2004

(54) PROCESS FOR THE PRODUCTION OF ACETIC ACID

(75) Inventor: Robert John Watt, Beverley (GB)

(73) Assignee: BP Chemicals Limited, London (GB)

( * ) Notice: Subject to any disclaimer, the term of this patent is extended or adjusted under 35 U.S.C. 154(b) by 422 days.

(21) Appl. No.: 09/702,056

(22) Filed: Oct. 31, 2000

(30) Foreign Application Priority Data

Nov. 12, 1999 (GB) .............................................. 9926855

(51) Int. Cl.[7] .............................................. C07C 51/12
(52) U.S. Cl. ........................ 562/519; 562/517; 562/232
(58) Field of Search ................................ 562/519, 517; 560/232

(56) References Cited

U.S. PATENT DOCUMENTS

| | | |
|---|---|---|
| 4,414,160 A | 11/1983 | Erpenbach et al. |
| 5,817,869 A | 10/1998 | Hinnenkamp et al. |
| 6,472,558 B1 * | 10/2002 | Key et al. .................... 562/519 |

FOREIGN PATENT DOCUMENTS

| | | |
|---|---|---|
| EP | 0 114 703 B1 | 10/1986 |
| EP | 0 749 948 A1 | 12/1996 |
| GB | 1 406 672 | 9/1975 |

OTHER PUBLICATIONS

Derwent Publications Ltd., London, GB; Class E16, AN 1978–50693A; XP002221883 & JP TE 063308 A; Mitsubishi Gas Chem. Ind. Co. Ltd.; Jun. 6, 1978 (abstract).

* cited by examiner

*Primary Examiner*—Alan L. Rotman
*Assistant Examiner*—Héctor M. Reyes
(74) *Attorney, Agent, or Firm*—Nixon & Vanderhye

(57) ABSTRACT

A process for the production of acetic acid by reacting carbon monoxide with methanol and/or a reactive derivative thereof in a liquid reaction composition comprising an iridium carbonylation catalyst, methyl iodide, methyl acetate, water and acetic acid characterised in that there is also present in the reaction composition a monodentate phosphine oxide compound in an amount of up to and including 200 mol per gram atom of iridium.

8 Claims, No Drawings

PROCESS FOR THE PRODUCTION OF ACETIC ACID

The present invention relates to a process for the production of acetic acid and in particular, to a process for the production of acetic acid by carbonylation in the presence of an iridium catalyst and methyl iodide co-catalyst.

Preparation of carboxylic acids by iridium-catalysed carbonylation processes is known and is described, for example in EP-A-0786447, EP-A0643034 and EP-A-0752406.

EP-A-0786447 describes a process for reacting carbon monoxide with a carbonylatable reactant and/or an ester derivative thereof in a liquid reaction composition comprising an iridium carbonylation catalyst, a hydrocarbyl halide, water and carbonylation reaction product, characterised in that the liquid reaction composition comprises water at a concentration of 2 to 8% by weight, hydrocarbyl halide at a concentration in the range 1 to 20% by weight and ester derivative of the carbonylatable reactant at a concentration in the range 1.0 to 60% by weight.

EP-A-0643034 describes a process for the production of acetic acid by carbonylation of methanol or a reactive derivative thereof which process comprises contacting methanol or a reactive derivative thereof with carbon monoxide in a liquid reaction composition in a carbonylation reactor characterised in that the liquid composition comprises (a) acetic acid, (b) an iridium catalyst, (c) methyl iodide, (d) at least a finite quantity of water, (e) methyl acetate and (f) as promoter, at least one of ruthenium and osmium.

EP-A-0752406 describes a process for the production of acetic acid comprising (1) continuously feeding methanol and/or a reactive derivative thereof and carbon monoxide to a carbonylation reactor which contains a liquid reaction composition comprising an iridium carbonylation catalyst, methyl iodide co-catalyst, a finite concentration of water, acetic acid, methyl acetate and at least one promoter; (2) contacting the methanol and/or reactive derivative thereof with the carbon monoxide in the liquid reaction composition to produce acetic acid; and (3) recovering acetic acid from the liquid reaction composition characterised in that there is continuously maintained in the liquid reaction composition throughout the course of the reaction (a) water at a concentration of no greater than 6.5% by weight, (b) methyl acetate at a concentration in the range 1 to 35% by weight and (c) methyl iodide at a concentration in the range 4 to 20% by weight.

The use of polydentate chelating phosphorus or arsenic ligands in carbonylation processes is known, for example from U.S. Pat. No. 4,102,920 and U.S. Pat. No. 4,102,921 which describe respectively, their use in rhodium and iridium catalysed carbonylation processes.

The use of phosphine oxide promoters in rhodium-catalysed carbonylation processes is known from U.S. Pat. No. 5,817,869 and from EP-A-0114703.

Thus, U.S. Pat. No. 5,817,869 relates to process for the production of acetic acid without the use of an alkali metal halide comprising contacting methanol or methyl acetate with carbon monoxide in the presence of a carbonylation system containing about 200 to about 1200 ppm of rhodium-containing component and a liquid reaction medium comprising about 20 to about 80 weight % acetic acid; from about 0.6 to about 36 weight % methyl iodide; from about 0.5 to about 10 weight % methyl acetate, said contacting being in the presence of at least one pentavalent Group VA oxide of the formula $R_3M=O$, which is present in a concentration of Group VA oxide to rhodium of greater than about 60:1, and water being added in an amount of from about 4 to about 12 weight %.

EP-A-0114703 relates to a process for the preparation of carboxylic acids and/or esters by reaction of an alcohol with carbon monoxide in the presence of a rhodium compound, an iodide and/or bromide source and a phosphorus, arsenic or antimony-containing compound as promoter, characterised in that the reaction is carried out in the presence of a compound of the formula

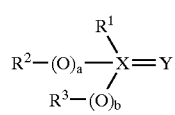

I wherein X represents phosphorus, arsenic or antimony and Y oxygen, sulphur or selenium and either a and b, independent of one another, are 0 or 1, $R^1$ represents hydrogen or an unsubstituted or substituted hydrocarbon group and $R^2$ and $R^3$ each represent an unsubstituted or substituted hydrocarbon group, or a and b are 0 and $R^2$ and $R^3$ together with X form a heterocyclic group and $R^1$ represents hydrogen or an unsubstituted or substituted hydrocarbon group, or in the presence of a complex of a compound of formula I with a hydrocarbon iodide or bromide, an acyl iodide or bromide or hydrogen iodide or bromide. Examples of compounds of formula I wherein a and b are 0, include triphenylphosphine oxide According to EP-A-0114703, the quantity of compound of formula I used as promoter in the process may vary within wide limits, for instance between 0.1 and 300 mol per gram atom rhodium. Preference is said to be given to use of 1–200, in particular 10–100 mol per gram atom rhodium. The promoters of EP-A-0114703 are directed towards improving the activity of the rhodium carbonylation catalyst system.

The technical problem to be solved is to provide an improved carbonylation process for the production of acetic acid. It has now been surprisingly found that by using a specified quantity of a monodentate phosphine oxide compound in an iridium-catalysed carbonylation process for the production of acetic acid, the quantities of by-product propionic acid, its precursors and derivatives produced are reduced and hence selectivity to the desired acetic acid is increased.

Thus, according to the present invention, there is provided a process for the production of acetic acid by reacting carbon monoxide with methanol and/or a reactive derivative thereof in a liquid reaction composition comprising an iridium carbonylation catalyst, methyl iodide, methyl acetate, water and acetic acid characterised in that there is also present in the reaction composition a monodentate phosphine oxide compound in an amount of up to and including 200 mol per gram atom of iridium.

The process of the present invention solves the technical problem defined above, by the use of a monodentate phosphine oxide compound in an amount of up to and including 200 mol per gram atom of iridium to reduce the amount of by-product propionic acid, its precursors such as ethyl iodide and ethyl acetate and its derivatives such as methyl propionate and ethyl propionate produced and increase the selectivity of the process to the desired acetic acid.

The monodentate phosphine oxide compound may be represented by the formula

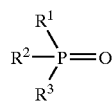
(II)

wherein $R^1$, $R^2$, $R^3$ are independently an unsubstituted or substituted $C_1$ to $C_{10}$ alkyl group or an unsubstituted or substituted $C_5$ to $C_{15}$ aryl group.

The $C_1$ to $C_{10}$ alkyl group may be straight or branched. Examples of suitable $C_1$–$C_{10}$ alkyl groups include methyl, ethyl, n-butyl and n-octyl. The $C_1$–$C_{10}$ alkyl group may be substituted by one or more substituents e.g. 1–4 substituents. Suitable substituents include $C_1$ to $C_{10}$ alkyl groups and $C_5$ to $C_{15}$ aryl groups.

The $C_5$–$C_{15}$ aryl group may be e.g. phenyl, alpha-naphthyl and beta-naphthyl, preferably phenyl. The $C_5$–$C_{15}$ group may be substituted with substituents selected from the group consisting of —$NO_3$, —OH, —CN, —$SO_3H$, —$OCH_3$ and —$CO_2H$.

A preferred monodentate phosphine oxide compound of formula II is triphenylphosphine oxide.

In the process of the present invention if at least one promoter is present in the reaction composition, higher concentrations of the monodentate phosphine oxide compound can be used, which enables the benefits of reduced by-product formation to be achieved at acceptable reaction rates. Suitable promoters are preferably selected from the group consisting of ruthenium, osmium, rhenium, cadmium, mercury, zinc, gallium, indium and tungsten, and are more preferably selected from the group consisting of ruthenium and osmium and most preferably is ruthenium. Preferably, the promoter is present in an effective amount up to the limit of its solubility in the liquid reaction composition and/or any liquid process streams recycled to the carbonylation reactor from the acetic acid recovery stage. The promoter is suitably present in the liquid reaction composition at a molar ratio of promoter:iridium in the range 0.5:1 to 15:1, preferably 0.5:1 to 10:1. Any reduction in carbonylation rate caused by the presence of the monodentate phosphine oxide compound may be off-set by increasing the concentration of promoter.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

The monodentate phosphine oxide compound may be present in the reaction composition in an amount of greater than 0.5 mol per grain atom of iridium. Preferably, the monodentate phosphine oxide compound is present in the reaction composition in an amount of 1 to 200 mol per gram atom of iridium when a promoter is present and is present in the reaction composition in an amount of 1 to 100 mol per gram atom of iridium when no promoter is present.

In the process of the present invention, the iridium carbonylation catalyst is preferably present in the liquid reaction composition at a concentration in the range 400 to 5000 ppm measured as iridium, more preferably in the range 500 to 3000 ppm measured as iridium. Any reduction in carbonylation rate caused by the presence of the monodentate phosphine oxide compound may be off-set by increasing the concentration of iridium catalyst, if present.

The iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form.

In the process of the present invention, the concentration of methyl iodide co-catalyst in the liquid reaction composition is preferably in the range 5 to 16% by weight.

In the process of the present invention, suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. In the process of the present invention the concentration of methyl acetate in the liquid reaction composition is preferably in the range 1 to 30% by weight, more preferably 5 to 25% by weight.

Water may be formed in situ in the liquid reaction composition, for example, by the esterification reaction between methanol reactant and acetic acid product. Small amounts of water may also be produced by hydrogenation of methanol to produce methane and water. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. The water concentration in the liquid reaction composition is suitably in the range 1–15 wt %, preferably in the range 1–6.5 wt %.

Preferably, the iridium- and promoter-containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating $I^-$ in the liquid reaction composition which has an adverse effect on the reaction rate. Some corrosion metal contaminants such as for example molybdenum have been found to be less susceptible to the generation of $I^-$. Corrosion metals which have an adverse affect on the reaction rate may be minimised by using suitable corrosion resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007, 130. Preferably, ionic contaminants are kept below a concentration at which they would generate 500 ppm $I^-$, preferably less than 250 ppm $I^-$ in the liquid reaction composition.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide feed and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than $1 \times 10^5$ N/m² partial pressure, more preferably less than $5 \times 10^4$ N/m² and yet more preferably less than $3 \times 10^4$ N/m². The partial pressure of carbon monoxide in the reactor is suitably in the range $1 \times 10^5$ N/m² to $7 \times 10^6$ N/m², preferably $1 \times 10^5$ N/m² to $3.5 \times 10^6$ N/m², more preferably $1 \times 10^5$ N/m² to $1.5 \times 10^6$ N/m².

The total pressure of the carbonylation reaction is suitably in the range $1 \times 10^6$ N/m² to $2 \times 10^7$ N/m², preferably $1.5 \times 10^6$ N/m² to $1 \times 10^7$ N/m², more preferably $1.5 \times 10^6$ N/m² to $5 \times 10^6$ N/m².

The temperature of the carbonylation reaction is suitably in the range 100 to 300° C., preferably in the range 150 to 220° C. Any reduction in carbonylation rate caused by the presence of the monodentate phosphine oxide compound may be off-set by increasing the reaction temperature.

The process of the present invention is preferably performed as a continuous process.

The acetic acid product may be recovered from the liquid reaction composition by withdrawing vapour and/or liquid from the carbonylation reactor and recovering acetic acid from the withdrawn material. Preferably, acetic acid is recovered from the liquid reaction composition by continuously withdrawing liquid reaction composition from the carbonylation reactor and recovering acetic acid from the withdrawn liquid reaction composition by one or more flash and/or fractional distillation stages in which the acetic acid is separated from the other components of the liquid reaction composition such as iridium catalyst, methyl iodide co-catalyst, promoter, methyl acetate, unreacted methanol, water and acetic acid solvent which may be recycled to the reactor to maintain their concentrations in the liquid reaction composition. To maintain stability of the iridium catalyst during the acetic acid product recovery stage, water in process streams containing iridium carbonylation catalyst for recycle to the carbonylation reactor should be maintained at a concentration of at least 0.5% by weight.

The process of the present invention may be performed a using carbonylation reaction conditions known in the art, for example as described in EP-A-0786447, EP-A-0643034, EP-A-0752406 and EP-A-0749948, the contents of which are hereby incorporated by reference.

The invention will now be illustrated by way of example only and with reference to the following examples:

GENERAL REACTION METHOD

A 300 cm³ zirconium autoclave, equipped with a stirrer and a liquid injection facility, was used for a series of batch autoclave experiments. The autoclave was flushed up to $5 \times 10^5$ N/m² with nitrogen and then flushed with carbon monoxide up to $5 \times 10^5$ N/m². An initial charge consisting of methyl acetate, acetic acid, methyl iodide and water, was placed into the autoclave. A catalyst solution was primed into a liquid injection line made up of (1.35 g) of $H_2IrCl_6$ aqueous solution (22.26% Ir w/w), water (5.0 g) and acetic acid (10.0 g). The resulting combined autoclave charge was thus methyl acetate (60.02 g), acetic acid (48.84 g), methyl iodide (23.77 g) and water (17.81 g). The contents of the autoclave were heated to 190° C. whilst being stirred at 1500 rpm. Once the temperature had reached 190° C. the $H_2IrCl_6$ catalyst solution was injected into the autoclave with an over-pressure of carbon monoxide to the hot autoclave to bring the autoclave pressure to $2.8 \times 10^6$ N/m².

The autoclave pressure and temperature were maintained at a constant $2.8 \times 10^6$ N/m² and 190° C. respectively throughout the reaction, until the uptake of carbon monoxide from a ballast vessel ceased. On termination of the reaction the autoclave was cooled and vented. After cooling and carefully venting the autoclave the liquid components were discharged and analysed for liquid products and by-products by known established gas chromatography methods.

Liquid by-products are determined by gas chromatography using a CB wax52 column on a Hewlett Packard 6820 Mk2 gas chromatograph. Detected components are quantified by integration of the component peaks relative to an external standard and expressed as parts per million (ppm) by weight.

The main liquid by-product from carbonylation of methanol to acetic acid is propionic acid. It's precursors (ethyl iodide and ethyl acetate) are also formed. In a continuous process these precursors would be recycled to the carbonylation reactor in recycle streams, building up to a steady state concentration at which the rate of their destruction to propionic acid balances their rate of removal. In a batch process, these precursors are not destroyed, but accumulate with the propionic acid in the liquid reaction composition and these can be measured at the end of the experiment. A reduction in the amount of propionic acid and its precursors measured at the end of a batch carbonylation experiment would be expected to indicate that in a continuous process, the amount of by-product propionic acid recovered with the acetic acid product would also be reduced.

In the batch reactions 'Total' propionic acid was defined as the sum of propionic acid and it's precursors ((ethyl acetate and ethyl iodide) converted to ppm propionic acid), detected in the quenched liquid products of the batch reaction and expressed in ppm.

Total propionic acid=ppm propionic acid+(ppm ethyl iodide×(74.08/155.97))+(ppm ethyl acetate×(74.08/88.11))

This represents the cumulative formation during the batch experiment of propionic acid and its precursors, ethyl iodide and ethyl acetate. Ethanol and acetaldehyde are produced in very small amounts such that they can be ignored.

The rate of gas uptake at a certain point in a reaction run was used to calculate the carbonylation rate, as number of moles of reactant consumed per liter of cold degassed reactor composition per hour (mol/l/hr), at a particular reactor composition (total reactor composition based on a cold degassed volume).

The methyl acetate concentration was calculated during the course of the reaction from the starting composition, assuming that one mole of methyl acetate was consumed for every mole of carbon monoxide that was consumed. No allowance was made for organic components in the autoclave headspace.

By monitoring the rate of carbonylation reaction and calculating the concentration of the reaction components during the experiment, it is possible to determine the rate of carbonylation reaction which would be expected if a carbonylation process were to be operated continuously whilst maintaining under steady state, a liquid reaction composition which is the same as the total reaction composition calculated at any particular point in the batch experiment. In the batch experiments the term 'reaction composition' refers to the total composition of the components in the autoclave in the cold degassed state. The principal difference between the batch experiments and continuous operation is that in the batch experiments, no allowance was made in calculating the component concentrations, for partitioning of the reaction components between the liquid and gaseous phases, Owing to this partitioning, the concentration of the reaction components present in the liquid phase in a batch reaction under reaction conditions was similar, but not identical, to the total reaction composition. In particular, the more volatile components in the reaction composition, such as methyl iodide and methyl acetate, were slightly less concentrated in the liquid reaction composition than in the total reaction composition, whereas the water concentration was comparable between the two. Therefore, the rate calculated in a batch experiment at a certain total reaction composition will be similar to that in a continuous process operating with a liquid composition which is the same as the batch total reaction composition. In addition, trends observed in batch experiments by varying the process variables, such as water concentration, were comparable with the trends observed in continuous experiments.

EXPERIMENT A

A baseline experiment was performed using 1.35 g of $H_2IrCl_6$ solution and a combined autoclave charged of methyl acetate (60.02 g), acetic acid (48.84 g), water (17.81 g) and methyl iodide (23.77 g).

The rate of reaction, based on carbon monoxide uptake was measured to be 10.04 mol/l/hr at a calculated reaction composition of 12.5% methyl acetate and steadily declined until virtually all the methyl acetate was consumed. Conversion to acetic acid was 98.2% based on methyl acetate consumed. Analysis of propionic acid precursors gave a total propionic acid make of 604 ppm. Gaseous by-products in the cold-vented off-gas were $H_2$, 1.94% v/v; $CO_2$, 2.24% v/v; $CH_4$, 3.67% v/v. Analysis of the final reaction composition by Gas Chromatography gave methyl iodide 13.8%; methyl acetate 0.59%; acetic acid 90.34%.

This is not an example according to the present invention because no monodentate phosphine oxide was present.

EXAMPLE 1

Experiment A was repeated except that the total combined autoclave charge consisted of methyl acetate (59.99 g), acetic acid (47.80 g), water (17.81 g) and methyl iodide (23.77 g). Triphenylphosphine oxide (43.40 g) was charged to the autoclave and 1.351 g of $H_2IrCl_6$ solution was used in the catalyst charge. The rate of reaction at a calculated reaction composition of 12.5% methyl acetate was measured as approx. 1.3 mol/l/hr. Conversion to acetic acid was 94.3% based on methyl acetate consumed. Analysis of the propionic acid precursors gave a total propionic acid make of 43 ppm. Gaseous by-products in the cold-vented off-gas were not measured due to a leak. Analysis of the final reaction composition by Gas Chromatography gave methyl iodide 1.65%; methyl acetate 41.1%; acetic acid 45.4%.

This is an example of the use of triphenylphosphine oxide at 200 mols. per gram atom of iridium catalyst and shows the reduction in liquid and gaseous by-products.

EXAMPLE 2

Experiment A was repeated except that the total combined autoclave charge consisted of methyl acetate (60.03 g), acetic acid (42.80 g), water (22.84 g) and methyl iodide (23.78 g). Triphenylphosphine oxide (10.85 g) was charged to the autoclave and 1.349 g of $H_2IrCl_6$ solution was used in the catalyst charge. The rate of reaction at a calculated reaction composition of 12.5% methyl acetate was measured as 3.57 mol/l/hr. Conversion to acetic acid was 82.7% based on methyl acetate consumed. Analysis of the propionic acid precursors gave a total propionic acid make of 185 ppm. Gaseous by-products in the cold-vented off-gas were $H_2$, 0.37% v/v/; $CO_2$, 3.53% v/v; $CH_4$, 8.5% v/v. Analysis of the final reaction composition by Gas Chromatography gave methyl iodide 3.8%; methyl acetate 5.75%; acetic acid 73.08%.

This is an example of the use of triphenylphosphine oxide at 50 mols per gram atom of iridium catalyst to reduce liquid and gaseous by-products.

EXAMPLE 3

Experiment A was repeated except the total combine autoclave charge consisted of methyl acetate (60.0 g), acetic acid (48.28 g), water (17.75 g) and methyl iodide (23.77 g). Triphenylphosphine oxide (2.16 g) was charged to the autoclave and 1.348 g of $H_2IrCl_6$ solution was used in the catalyst charge. The rate of reaction at a calculated reaction composition of 12.5% methyl acetate was measured as 6.60 mol/l/hr. Conversion to acetic acid was 92.2% based on methyl acetate consumed. Analysis of the propionic acid precursors gave a total propionic acid make of 278 ppm. Gaseous by-products in the cold-vented off-gas were $H_2$, 0.94% v/v; $CO_2$, 2.57% v/v; CH4, 5.94% v/v. Analysis of the final reaction composition by Gas Chromatography gave methyl iodide 1.91%; methyl acetate 2.67%; acetic acid 78.42%.

This is an example of the use of triphenylphosphine oxide at 10 mols per gram atom of iridium catalyst to reduce liquid and gaseous by-products.

EXAMPLE 4

Experiment A was repeated except the total combined autoclave charge consisted of methyl acetate (60.01 g), acetic acid (47.79 g), water (17.85 g) and methyl iodide (23.77 g). Triphenylphosphine oxide (0.22 g) was charged to the autoclave and 1.349 g of $H_2IrCl_6$ solution was used in the catalyst charge. The rate of reaction at a calculated reaction composition of 12.5% methlyl acetate was measured as 10.3 mol/l/hr. Conversion to acetic acid was 98.5% based on methyl acetate consumed. Analysis of the propionic acid precursors gave a total propionic acid make of 412 ppm. Gaseous by-products in the cold-vented off-gas were $H_2$, 1.58% v/v; $CO_2$, 2.42% v/v; $CH_4$, 5.21% v/v. Analysis of the final reaction composition by Gas Chromatography gave methyl iodide 11.6%; methyl acetate 0.51%; acetic acid 88.95%.

This is an example of the use of triphenylphosphine oxide at 1 mols per gram atom of iridium catalyst to reduce liquid and gaseous by-products.

EXPERIMENT B

A baseline experiment was performed repeating Experiment A except the total combined autoclave charge consisted of methyl acetate (60.0 g), acetic acid (44.58 g), water (18.71 g), methyl iodide (12.45 g) and $Ru(CO)_4I_2$ (3.64 g).

1.34 g of H$_2$IrCl$_6$ solution was used in the catalyst charge. The rate of reaction at a calculated reaction composition of 12.5% methyl acetate was measured as 25.94 mol/l/hr. Conversion to acetic acid was 97.1% based on methyl acetate consumed. Analysis of the propionic acid precursors gave a total propionic acid make of 293 ppm. Gaseous by-products in the cold-vented off-gas were H$_2$, 2.42% v/v; CO$_2$, 2.9% v/v; CH$_4$, 5.63% v/v. Analysis of the final reaction composition by Gas Chromatography gave methyl iodide 0.831%; methyl acetate 1.0%; acetic acid 82.42%.

This is not an example according to the present invention because no monodentate phosphine oxide was present.

EXAMPLE 5

Experiment B was repeated except that the total combined autoclave charge consisted of charge consisted of methyl acetate (60.03 g), acetic acid (54.53 g), water (18.80 g), methyl iodide (12.43 g), Ru(CO)4I$_2$ (3.70 g ) and triphenylphosphine oxide (0.44 g). 1.341 g of H$_2$IrCl$_6$ solution was used in the catalyst charge. The rate of reaction at a calculated reaction composition of 12.5% methyl acetate was measured as 25.65 mol/l/hr. Conversion to acetic acid was 96.7% based on methyl acetate consumed. Analysis of the propionic acid precursors gave a total propionic acid make of 283 ppm. Gaseous by-products in the cold-vented off-gas were H$_2$, 2.18% v/v; CO$_2$, 2.88% v/v; CH$_4$, 5.75% v/v/. Analysis of the final reaction composition by Gas Chromatography gave methyl iodide 0.01%; methyl acetate 1.16%; acetic acid 79.8%.

This is an example of the use of triphenylphosphine oxide at 1 mols per gram atom of iridium catalyst in presence of 5 mols ruthenium promoter per gram atom of iridium to reduce liquid and gaseous by-products.

EXAMPLE 6

Experiment B was repeated except that the total combined autoclave charge consisted of methyl acetate (60.02 g), acetic acid (49.61 g), water (8.72 g), methyl iodide (12.44 g), Ru(CO)$_4$I$_2$ (3.65 g) and triphenylphosphine oxide (2.17 g). 1.346 g of H$_2$IrCl$_6$ solution was used in the catalyst charge. The rate of reaction at a calculated reaction composition of 12.5% methyl acetate was measured as 20.37 mol/l/hr. Conversion to acetic acid was 94.7% based on methyl acetate consumed. Analysis of the propionic acid precursors gave a total propionic acid make of 158 ppm. Gaseous by-products in the cold-vented off-gas were H$_2$, 0.82% v/v; CO$_2$, 2.95% v/v; CH$_4$, 5.44% v/v. Analysis of the final reaction composition by Gas Chromatography gave methyl iodide 0.04%; methyl acetate 1.85%; acetic acid 78.4%.

This is an example of the use of triphenylphosphine oxide at 5 mols per gram atom of iridium catalyst in presence of 5 mols ruthenium promoter per gram atom of iridium to reduce liquid and gaseous by-products.

The results are summarised in the Table below.

Note: Since propionic acid formation increases rapidly above 90% conversion of methyl acetate in iridium and iridium/ruthenium catalysed carbonylations, more accurate comparisons from batch reactions are found in experiments that are terminated below 90% conversion.

TABLE

| Example/ Experiment | Catalyst system | Additive | Propionic acid make (ppm) | Conversion (%) | Reaction rate at 12.5% methyl acetate mol/l/hr | Comments |
| --- | --- | --- | --- | --- | --- | --- |
| Experiment A | Ir | none | 604 | 98.2% | 10.04 | |
| Example 1 | Ir | triphenylphosphine oxide | 43 | 94.3% | 1.3 | Reduced rate but reduced propionic acid. |
| Example 2 | Ir | triphenylphosphine oxide | 185 | 82.7 | 3.57 | Reduced rate but reduced propionic acid. |
| Example 3 | Ir | triphenylphosphine oxide | 278 | 92.2% | 6.6 | Reduced rate but reduced propionic acid |
| Example 4 | Ir | triphenylphosphine oxide | 412 | 98.5% | 10.3 | Good rate and reduced propionic acid |
| Experiment B | Ir/Ru | none | 293 | 97.1% | 25.94 | |
| Example 5 | Ir/Ru | triphenylphosphine oxide | 283 | 96.7% | 25.65 | Good rate and propionic acid remains low |
| Example 6 | Ir/Ru | triphenylphosphine oxide | 158 | 94.7% | 20.37 | Reduced rate but reduced propionic acid |

I claim:

1. A process for the production of acetic acid which comprises reacting carbon monoxide with a reactant selected from the group consisting of methanol, reactive derivatives of methanol and mixtures thereof in a liquid reaction composition comprising an iridium carbonylation catalyst, methyl iodide, methyl acetate, water and acetic acid wherein there is also present in the reaction composition a monodentate phosphine oxide compound in an amount up to and including 200 mol per gram atom of iridium.

2. A process according to claim 1 wherein the monodentate phosphine oxide compound is present in the reaction composition in an amount of greater than 0.5 mol per gram of iridium.

3. A process according to claim 1 wherein the monodentate phosphine oxide compound is represented by the formula:

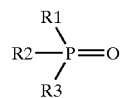

wherein R1, R2, R3 are independently an unsubstituted or substituted C$_1$ to C$_{10}$ alkyl group or an unsubstituted or substituted C$_5$ to C$_{15}$ aryl group.

4. A process according to claim 1 wherein the reaction composition further comprises at least one promoter.

5. A process according to claim 4 wherein the at least one promoter is selected from the group consisting of ruthenium, osmium, rhenium, cadmium, mercury, zinc, gallium, indium and tungsten.

6. A process according to claim 2 wherein the reaction composition further comprises at least one promoter.

7. A process according to claim 6 wherein the at least one promoter is selected from the group consisting of ruthenium, osmium, rhenium, cadmium, mercury, zinc, gallium, indium and tungsten.

8. A process according to claim 4 wherein the monodentate phosphine oxide compound is present in the reaction composition in an amount of 1 to 200 mol per gram atom of iridium.

* * * * *